(12) United States Patent
Galen et al.

(10) Patent No.: US 11,053,473 B2
(45) Date of Patent: Jul. 6, 2021

(54) EXTERNAL SONICATION

(71) Applicant: HEMEX HEALTH, INC., Portland, OR (US)

(72) Inventors: Peter Galen, Portland, OR (US); James Daren Bledsoe, Portland, OR (US); Jered Wikander, Portland, OR (US); Steven M. Goss, Salem, OR (US)

(73) Assignee: HEMEX HEALTH, INC., Portland, OR (US)

( * ) Notice: Subject to any disclaimer, the term of this patent is extended or adjusted under 35 U.S.C. 154(b) by 0 days.

(21) Appl. No.: 16/912,175

(22) Filed: Jun. 25, 2020

(65) Prior Publication Data
US 2020/0407676 A1 Dec. 31, 2020

Related U.S. Application Data

(60) Provisional application No. 62/866,468, filed on Jun. 25, 2019.

(51) Int. Cl.
| | |
|---|---|
| *B01F 11/02* | (2006.01) |
| *C12M 1/42* | (2006.01) |
| *C12M 1/34* | (2006.01) |
| *C12N 13/00* | (2006.01) |

(52) U.S. Cl.
CPC ......... *C12M 35/04* (2013.01); *B01F 11/0283* (2013.01); *B01F 11/0291* (2013.01); *C12M 41/12* (2013.01); *C12N 13/00* (2013.01)

(58) Field of Classification Search
CPC .................................................. B01F 11/0291
USPC ....................................................... 366/116
See application file for complete search history.

(56) References Cited

U.S. PATENT DOCUMENTS

| | | | | | |
|---|---|---|---|---|---|
| 3,584,327 | A | * | 6/1971 | Murry | G10K 11/24 15/104.16 |
| 3,591,862 | A | * | 7/1971 | Winston | B06B 3/00 310/322 |
| 3,614,069 | A | * | 10/1971 | Murry | B01J 19/10 366/119 |
| 3,636,859 | A | * | 1/1972 | Null | F24C 7/00 99/348 |
| 4,107,790 | A | * | 8/1978 | McCord | B08B 3/12 366/127 |
| 4,562,413 | A | | 12/1985 | Mishiro et al. | |

(Continued)

FOREIGN PATENT DOCUMENTS

| | | |
|---|---|---|
| WO | 0130304 A1 | 5/2001 |
| WO | 2005111614 | 11/2005 |

OTHER PUBLICATIONS

International Search Report and Written Opinion dated Jan. 7, 2020, International Application No. PCT/US19/56832, International Filing Date Oct. 17, 2019.

(Continued)

*Primary Examiner* — David L Sorkin
(74) *Attorney, Agent, or Firm* — Lane Powell PC

(57) ABSTRACT

External sonication, which is a technique by which ultrasonic energy is applied externally to a cartridge containing the sample, is contemplated herein. External sonication can be performed by a sonicator external to a sample contained within a cartridge. The cartridge can include sonication particles to enhance sonication or cavitation within the sample. A sonication algorithm can also be used to increase sonication efficiency.

26 Claims, 9 Drawing Sheets

(56) References Cited

U.S. PATENT DOCUMENTS

| | | | |
|---|---|---|---|
| 5,468,616 | A | 11/1995 | Coulter et al. |
| 5,484,573 | A * | 1/1996 | Berger .................... B01J 19/10 366/108 |
| 5,853,994 | A | 12/1998 | Gopinathan et al. |
| 6,736,535 | B2 * | 5/2004 | Halsall ................ B01F 11/0258 122/19.1 |
| 6,984,989 | B2 | 1/2006 | Kudo et al. |
| 7,134,341 | B2 | 11/2006 | Girmonsky et al. |
| 2002/0009015 | A1 * | 1/2002 | Laugharn, Jr. ........... B01J 19/10 366/108 |
| 2003/0234642 | A1 | 12/2003 | Clegg et al. |
| 2005/0163716 | A1 | 7/2005 | Unger et al. |
| 2006/0024803 | A1 * | 2/2006 | Berlien ................. C12M 35/04 435/173.5 |
| 2006/0196915 | A1 | 9/2006 | Gunnerman |
| 2007/0055161 | A1 | 3/2007 | Garg et al. |
| 2008/0033296 | A1 | 2/2008 | Isern |
| 2013/0289371 | A1 | 10/2013 | Debreczeny et al. |
| 2014/0001058 | A1 | 1/2014 | Ghaffari et al. |
| 2014/0276754 | A1 | 9/2014 | Gilbert et al. |
| 2016/0030007 | A1 | 2/2016 | Tsujita |
| 2016/0216284 | A1 | 7/2016 | Misener et al. |
| 2018/0064384 | A1 | 3/2018 | Galen et al. |
| 2018/0224472 | A1 | 8/2018 | Loo et al. |

OTHER PUBLICATIONS

International Search Report and Written Opinion dated Sep. 21, 2020, International Application No. PCT/US2020/039623, International Filing Date Jun. 25, 2020.

* cited by examiner

EXTERNAL SONICATION

CROSS-REFERENCE TO RELATED APPLICATIONS

This application claims the benefit of U.S. Provisional Patent Application Ser. No. 62/866,468, filed Jun. 25, 2019, the contents of which are herein incorporated by reference in their entirety.

BACKGROUND

Patient diagnostic services save lives, reduce the time to treatment for the patient and provide valuable insight for targeted treatment. In many developed countries, modern medical facilities can provide patients with the most advanced diagnostic services, which allows patients to be efficiently and effectively treated. In less developed countries or regions, high quality medical facilities and diagnostic services can be lacking, often due to economic and infrastructure considerations. In many less developed countries, the economy cannot afford the latest in medical technology and infrastructure, such as a robust power grid or highly trained clinicians, required to support the high demands of modern medical technology. Sadly, a large portion of the world's population resides in underserved or underdeveloped areas where the lack of efficient and effective diagnostic services critically impacts the population morbidity, mortality and overall health. This lack of medical care can lead or contribute to knock-on effects, such as low economic and educational development.

Often, many less developed countries and areas also lack sufficient trained users that are typically required to perform the necessary diagnostic services. This can lead to inconclusive or erroneous results from diagnostic services or to significant delays in diagnosis as the diagnostic services are required to be performed in another location that has the requisite infrastructure and/or knowledge to perform the diagnostic service. For patients, this can mean increased time and cost of transport leading to further delays in treatment, which can decrease their chances of survival, increase the spread of the disease, and/or lead to increased debilitation caused by the disease or condition.

Where large laboratories may be prohibitively expensive and difficult to staff, diagnostic devices may provide an effective solution. Such a solution could provide timely, accurate, and cost-effective health care.

One of the treatable common ailments effecting less developed countries are hemoglobin disorders, such as sickle cell disease (SCD), thalassemias and other hemoglobinopathies. These are genetic disorders that are believed to have evolved in response to malaria. With population migration, these conditions have spread to the global population and affect the livelihood and health of a large number of people. With early detection or diagnosis, these conditions can be treated and managed before they have significant adverse impacts on the stricken individual. As with malaria, these disorders affect the populations of less developed countries and areas, which have limited to no access to the diagnostic services to rapidly, effectively and efficiently diagnose the conditions.

The devices can perform the diagnostic service or test on a blood sample. The blood sample may need to undergo processing in a certain manner so that the device can properly analyze the sample. For example, one or more components of the blood sample may need to be lysed to release components in the sample, to release a first component from a second component to analyze the first component, or the like.

Current sonication systems and methods disrupt components of the sample and include direct sonication (i.e., a sonication probe is immersed into and in contact with the sample) and wet sonication (i.e., sonication bath where the sample is placed in a container and then that container is partially immersed in an ultrasonic bath). Each implementation has its own drawbacks—some of which include sample size, lack of energy focus, potential contamination issues, excessive heat, and the like. The volume or size of the sample directly impacts the amount of ultrasonic energy required for total disruption. The fluid viscosity also impacts energy transfer—more viscous samples require more ultrasonic energy which can result in heat generation. Excessive heat generated can damage or destroy the sample being tested.

What is needed is a system or method for effective sample lysing or disruption.

DETAILED DESCRIPTION

Figure 1A:
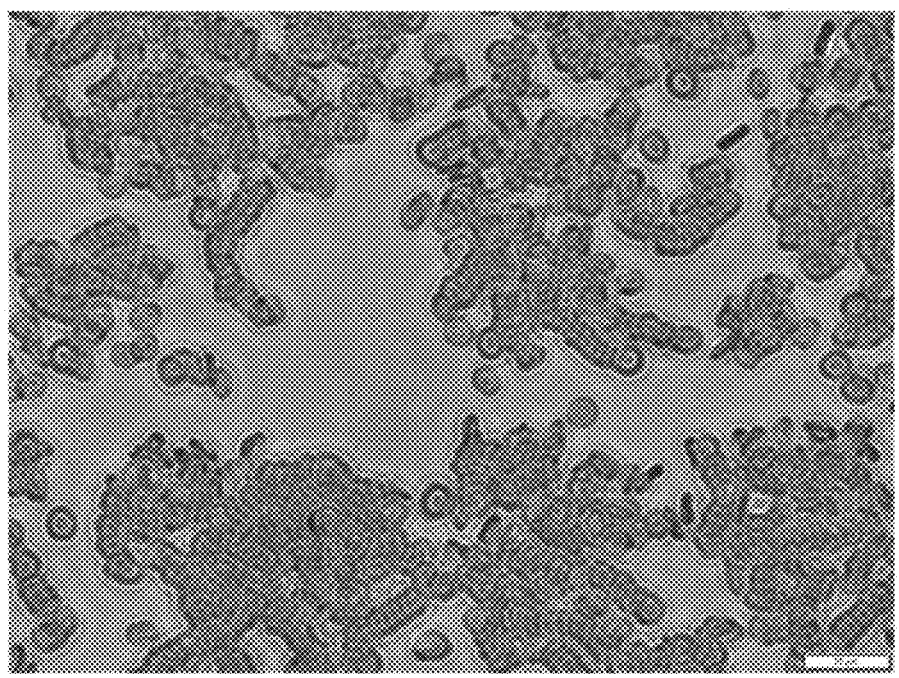
FIG. 1A illustrates a sample before sonication.

Sonication is the act of applying sound energy to agitate particles or components within a sample or medium. During sonication, kinetic energy from the sound oscillation generated from a sonicator creates heat and cavitation bubbles. When this oscillation energy is effectively applied to the sample, the heat and/or cavitation bubbles (i.e., the forming and bursting of the bubbles) agitate and disrupt the sample components. The volume or size of the sample directly impacts the amount of ultrasonic energy required for total disruption. The fluid viscosity also impacts energy transfer—more viscous samples require more ultrasonic energy.

The blood sample may need to undergo processing in a certain manner so that the device can properly analyze the sample. The device can be used in a traditional lab setting, in the field (i.e., point-of-care), or the like. Sonication can lyse a first component of the blood sample thereby releasing a second component of the blood sample. For example, red blood cells can be lysed to release hemozoin. The blood sample, into which the hemozoin has been released, can undergo analysis to determine level of infection, type of infection, the like, or combinations or multiples thereof.

Additionally, a blood sample within a lab or lab-type setting may need to undergo processing for proper analysis. Sonication can be used to remove a component from the blood sample, such as red blood cells, without using a reagent that can affect downstream results. For example, certain reagents can affect whole genome analysis, next generation sequencing, polymerase chain reaction, or the like. Sonicating the sample to lyse the red blood cells, rather than using a reagent, permits the sample to be properly analyzed in one or more downstream steps.

External sonication is a technique by which ultrasonic energy is applied externally to a cartridge containing the sample. In one embodiment, the cartridge can be sealed or unsealed. The cartridge used can be one that is commercially available or one which is custom designed. External sonication is effective in maximizing sample content disruption while optimizing energy transfer into the sample, minimizing heat generation in the sample, minimizing heat and energy dissipation into the sample.

The ultrasonic energy of external sonication passes through the cartridge walls into the sample, thereby inducing pressure variations causing cavitation bubbles that grow and collapse—the sound waves are transformed into mechanical energy. The mechanical energy that is dissipated into the sample results in effective sample content disruption without requiring any sonication probe in direct contact with the sample fluid. Effective external sonication, for example, maximizes sample content disruption while optimizing energy transfer into the sample, minimizing heat generation in the sample, and minimizing heat and energy dissipation in the external sonication system. External sonication can be used for any appropriate sample. More specifically, some applications of external sonication include, without limitation, working with hazardous sample sources, cellular disruption for virus release in a closed system, DNA fragmentation, and heating/mixing/agitating solutions. In the following description, the term "resonate point" is used to describe a point or location on or within a system or a point or location on or within a component of a system, which produces resonance. The resonance can be a resonant frequency. The resonance can be electrical or mechanical. For example, with mechanical resonance, components of a blood sample absorb more energy from a sonicator, such as an external sonicator, when the sonicator applies oscillations at a frequency that matches the natural frequency of the components.

In the following description, the term "sample" is used to describe at least one material to undergo testing, processing, combinations thereof, or the like. The sample can be inorganic, plant-based, organism-based, or animal-based. For example, the sample can be derived or obtained from a plant, algae, mineral, or the like. As another example, the sample, such as one derived or obtained from an organism, an animal, or a human, can a biological fluid, a biological semi-solid, a biological solid which can be liquefied in any appropriate manner, a suspension, a portion of the suspension, a component of the suspension, or the like. For the sake of convenience, the sample referenced is whole blood, though it should be understood that the method and system described and discussed herein is used with any appropriate sample, such as urine, blood, bone marrow, buffy coat, cystic fluid, ascites fluid, stool, semen, cerebrospinal fluid, nipple aspirate fluid, saliva, amniotic fluid, mucus membrane secretions, aqueous humor, vitreous humor, vomit, vaginal fluid, and any other physiological fluid or semi-solid. For example, the sample is a tissue sample or a material from adipose tissue, an adrenal gland, bone marrow, a breast, a caudate, a cerebellum, a cerebral cortex, a cervix, a uterus, a colon, an endometrium, an esophagus, a fallopian tube, a heart muscle, a hippocampus, a hypothalamus, a kidney, a liver, a lung, a lymph node, an ovary, a pancreas, a pituitary gland, a prostate, a salivary gland, a skeletal muscle, skin, a small intestine, a large intestine, a spleen, a stomach, a testicle, a thyroid gland, or a bladder.

In the following description, the term "sonication particle" is used to describe an object or entity to increase or enhance sonication, cavitation, or both of a sample by an external sonication system. The sonication particle can be a bead, a rod, a nanoparticle, a microsphere, or the like. The sonication particle can be composed of a metal, silica, glass, a polymer, the like, or combinations or multiples thereof. When multiple sonication particles are used, the sonication particles can have the same characteristics or at least two sonication particles can have one or more different characteristic (e.g., size, shape, material, surface functionalization, surface depressions or dimples, or the like).

Figure 1B:
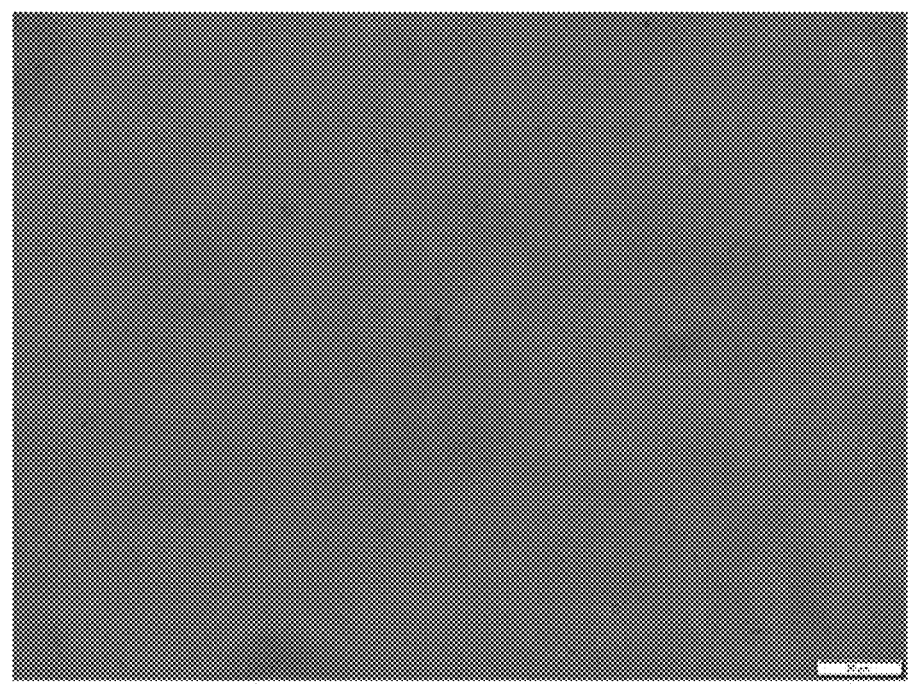
FIG. 1B illustrates the sample after sonication.

FIG. 1A shows a sample before external sonication (i.e., blood cells of the sample are intact). FIG. 1B shows the sample after external sonication. As can be seen in FIG. 1B, external sonication decreased the opacity of the sample. Though the opacity of blood can be decreased by external sonication, other types of patient samples can have the opacity remain the same or increase.

External sonication disrupts the blood cells of the sample, thereby causing the cellular contents, including the malaria parasite, to be released into the sample medium by breaking or lysing the membranes of the blood cells. The malaria parasite is also disrupted thereby causing the release of the parasite food vacuoles into the sample medium; these food vacuoles are then disrupted which causes the release of hemozoin clumped crystals; the clumped crystals are disrupted by breaking the lipid bonds, thereby resulting in less crystal clumping and individual crystals being freed into the sample medium.

The effectiveness of the external sonication can be further enhanced by optimizing ultrasonic energy transfer efficiency (e.g., frequency, resonate point of an external sonicator system, amount of energy available to be transferred, temperature, amount of time energy is being transferred; by controlling or adjusting the sample volume, chemistry, or viscosity, such as by adding reagents (e.g., deionized water, detergents, surfactants, defoaming agent, stains (e.g., fluorescent, chromogenic, or the like), or the like) to the sample to dilute the sample, change the difficulty of disrupting a component, or to reduce residual bubbles within the sample; by adding additional material, such as the one or more sonication particles, that can seed the start of the cavitation process; by controlling applied voltage of an ultrasonic transducer (fixed or variable); by controlling the current of the ultrasonic transducer (fixed or variable); by controlling the frequency of the ultrasonic transducer (fixed or variable); by controlling the on/off time of the voltage; by controlling the on/off time of the current; or by controlling the on/off time of the ultrasonic transducer (fixed or variable). Furthermore, the reagents can be used in downstream processing or are compatible with further downstream processing. In one aspect, a more effective external sonication allows for a reduced ultrasonic energy to be used to disrupt the contents of the sample.

Figure 2:
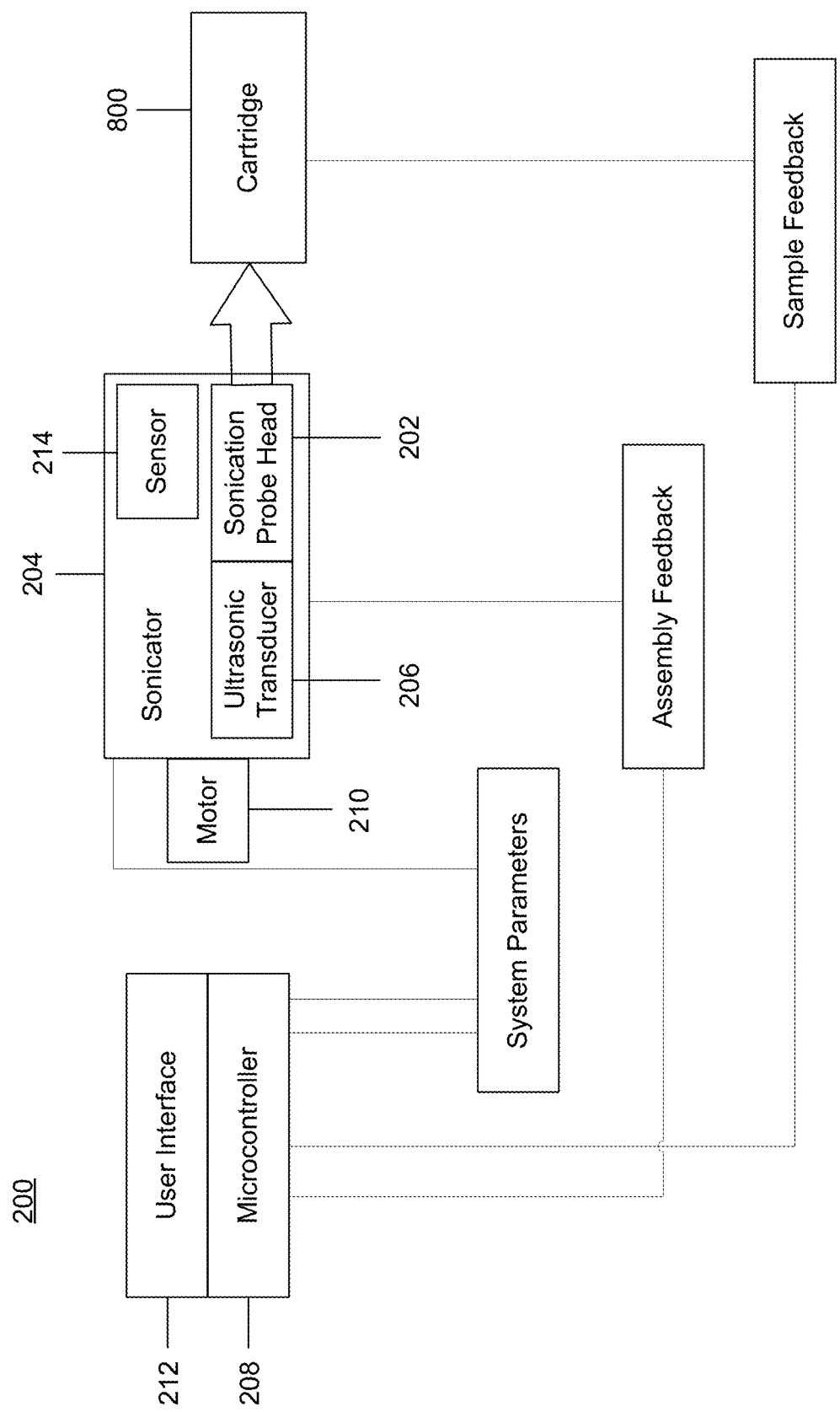
FIG. 2 is a block diagram of an example external sonicator system.

FIG. 2 shows a block diagram for an external sonicator system 200. First, a sample is provided in the cartridge 800. The sample, prior or subsequent to being added to the cartridge 800, can be processed, such as by adding one or more reagents including, without limitation, magnetic nanoparticles, non-magnetic solids, surfactants, defoaming agent, permeabilizing agents, deionized water, diluents, detergents, alcoagitathols (e.g., isopropyl alcohol), biocide, stains/labels, combinations thereof, or the like.

The cartridge 800 is then placed in contact with or is inserted into a probe head 202 of a sonicator 204. The sonicator 204 includes an ultrasonic transducer 206, which generates ultrasonic energy or ultrasonic sound waves, coupled to the probe head 202, which transmits the ultrasonic energy or ultrasonic sound waves to the cartridge 800. The ultrasonic energy or ultrasonic sound waves then travel into the sample held within the cartridge 800. To start the transfer of the ultrasonic energy into the cartridge 800, the voltage applied to the ultrasonic transducer 206 is varied in either a fixed or random frequency around the resonate point of the external sonicator system 200. In one embodiment, the ultrasonic transducer 206 is coupled to the probe head 202 in a manner that does not dampen the available energy for transfer or change the resonate point with, for example, stiffened connections, stiffened supports, dampeners, combinations thereof, or the like.

The probe head 202 design focuses energy transfer to and through a wall of the cartridge 800. The probe head 202 design also increases or decreases energy transfer to and through the wall of the cartridge 800. The design of the probe head 202 can also be selected to maximize contact area with the cartridge 800. The design of the probe head 202 transfers ultrasonic energy across one or more surfaces of the cartridge 800 or transfers ultrasonic energy across a plurality of cartridges (i.e., the probe head 202 can work with a plurality of cartridges, cartridge shapes, cartridge configurations, etc.).

A characteristic of the probe head 202 (e.g., length, material, diameter, or both) can be selected to match the resonate point of the ultrasonic transducer. For example, the length of the probe head 202 can be determined by the sonicator frequency. A longer probe head produces a longer wavelength, which is the inverse of frequency (i.e., frequency=1/wavelength). Therefore, the length of the probe head 202 can be inversely proportional to or matched to the sonicator frequency (i.e., the probe head 202 is shorter for a higher frequency).

Different materials have different resonate points. The resonate point of a material can be determined by the material density, the elastic modulus, or both.

The shape, size, or contact area of the probe head 202 can be selected to optimize or more efficiently focus or disperse the ultrasonic energy to the sample based on one or more characteristics of the walls of the cartridge 800 (e.g., material, thickness, shape, area, radius, curves, corners, combinations thereof, or the like). For example, a probe head having a shape that is contoured to the cartridge to have more contact area and fewer air gaps between the probe head and wall can transmit ultrasonic energy more efficiently than a probe head which has less contact area and more air gaps with the wall of the cartridge. As another example, a larger probe head can have greater surface area, thereby having greater energy transmission than a smaller probe head.

Figure 3A:
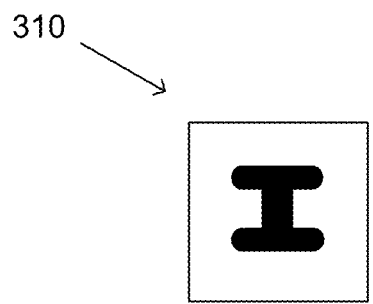
FIGS. 3A-3D illustrate example probe heads.
Figure 3B:
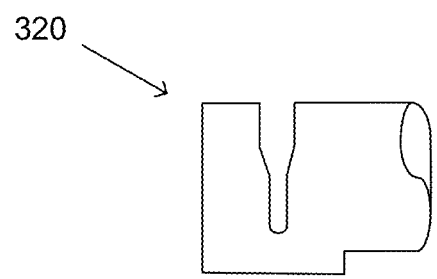

FIGS. 3A-3B show example probe heads into which the cartridge can be inserted. The cartridge can be sized and shaped to fit within an opening or a cutout of the probe head. For example, probe heads include a block with an I-shaped cutout extending there through 310 (FIG. 3A) and a block with a tapered, V-shaped, or bottle-shaped cutout extending there through 320 (FIG. 3B). A portion of the cartridge can be tapered thereby being able to fit within a tapered cutout, or a portion of the cartridge can be rectangular thereby being able to fit within a middle portion of an I-shaped cutout. The cartridge can be inserted into the probe heads by placing the cartridge into the cutout or opening of the probe head. Alternatively, the cutout or opening of the probe head can be slid over or placed on top of the cartridge.

Figure 3C:
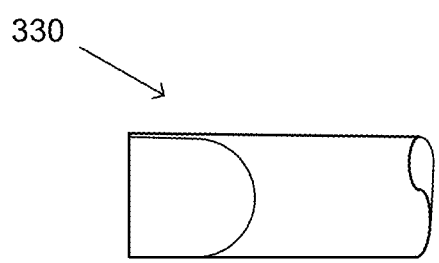
Figure 3D:
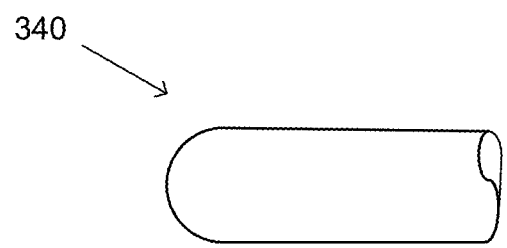

FIGS. 3C-3D show example probe heads that contact the cartridge external surface(s). A tip of the probe head or a side of the probe head can contact an external wall of the cartridge. Example probe heads include partially tapered tip with a flat or chisel-shaped face 330 (FIG. 3C), a rod or hemispherical 340 (FIG. 3D).

Returning again to FIG. 2, the sonicator 204 is controlled by a microcontroller 208 which is programmed to control one or more parameters of the external sonication system 200 to generate effective content disruption of the sample within the cartridge 800, to determine how the sample changes before, during, and after the sonication, or to provide real time control and feedback. In one embodiment, the microcontroller 208 is electrically coupled to the ultrasonic transducer 206 of the sonicator 204. Variable control, for example, allows for automated adjustments that adjust for potential drift of control parameters during use and over time that would impact disruption effectiveness.

The microcontroller 208 controls the one or more parameters of the external sonication system 200 based on at least one of location of the external sonicator relative to a cartridge wall, contact pressure of the probe head, sample sonication feedback, user input settings, and manufacturing assembly feedback. The user input can be obtained via a user interface 212, so as to receive input, such as instructions, sample information, patient information, or the like, or to output results, data, or other information. The user interface can be a display, such as a screen, such as a touchscreen, lights, or other visual indicators. The touchscreen used to display information, such as analysis results, to the user can also be used by a user to input to the external sonication system 200. An audible output can include a speaker, buzzer, or other audible indicators. The output, visual and/or audible, can be output through an external device, such as a computer, speaker, or mobile device connected physically or wirelessly to the external sonication system 200. The user interface 212 can include tactile prompts, input, and output. The output, whether visual, audible, or tactile, can output data, including the collected analysis data and interpretative data indicative of diagnosis, including the presence or absence of an infection, disease, or condition within the patient or the patient sample. An example can include the presence of hemozoin within the patient sample. The interpretive data output can be based on the analysis data collected and processed by processing circuitry of the external sonication system 200.

The parameters controlled by the microcontroller 208 and the assembly and sample feedback provided to the microcontroller 208 include, without limitation, voltage, current, frequency, position, probe head position (e.g., touching or not touching the cartridge), probe head contact force, temperature, time, probe head temperature, sound generation during the external sonication process, sample opacity, sample temperature, and sample agitation. The microcontroller 208 controls the one or more parameters through hardware or software. The microcontroller 208 can apply the parameters by maintaining a constant value (e.g., maintaining the same voltage or frequency), stepping, ramping, the like, or combinations or multiples thereof. For example, the microcontroller 208 can control temperature of the ultrasonic transducer, the sample, or the ultrasonic transducer and the sample by reducing voltage or current to the ultrasonic transducer 206 during the external sonication process; pulsing the voltage or current on and off to the ultrasonic transducer 206; or, to running the ultrasonic transducer 206 until the temperature exceeds a heat threshold, then turning the voltage or current off to the ultrasonic transducer 206 until temperature reaches a cool threshold, then repeating until the external sonication process is completed. As another example, the microcontroller 208 controls the time of external sonication to the ultrasonic transducer, via software or firmware, to continue with the sonication process for an additional amount of time or to discontinue the sonication process at a shorter time duration. Alternatively, though a microcontroller is discussed, the external sonicator system 200 can include one or more of a processor/microprocessor, memory, or programmable input/output peripherals.

The microcontroller 208 can also control the movement of the sonicator 204 along one or more axes by a motor 210. The motor 210 can be a servomotor, a stepper motor, an actuator (e.g., piezoelectric, electric, pneumatic, mechanical, linear, or rotary), a solenoid, or any appropriate device for providing motion along at least one axis. In one embodiment, the motor 210 is coupled to a housing (not shown). In one embodiment, the motor 210 is coupled to the ultrasonic transducer 206.

The sonicator 204 can also include a sensor 214 to determine the force applied to or on the probe head 202 (e.g., based on contact with the cartridge) or to determine the distance between the probe head 202 and the cartridge 800 so as to not overtravel (i.e., traveling past a desired point of contact) or under travel (i.e., not traveling to the desired point of contact). The sensor 214 can be mechanical (e.g., a switch), electrical (e.g., a linear encoder), capacitive, optical (e.g., a laser), acoustic, inductive (e.g., a linear variable differential transformer), or the like.

Figure 4:
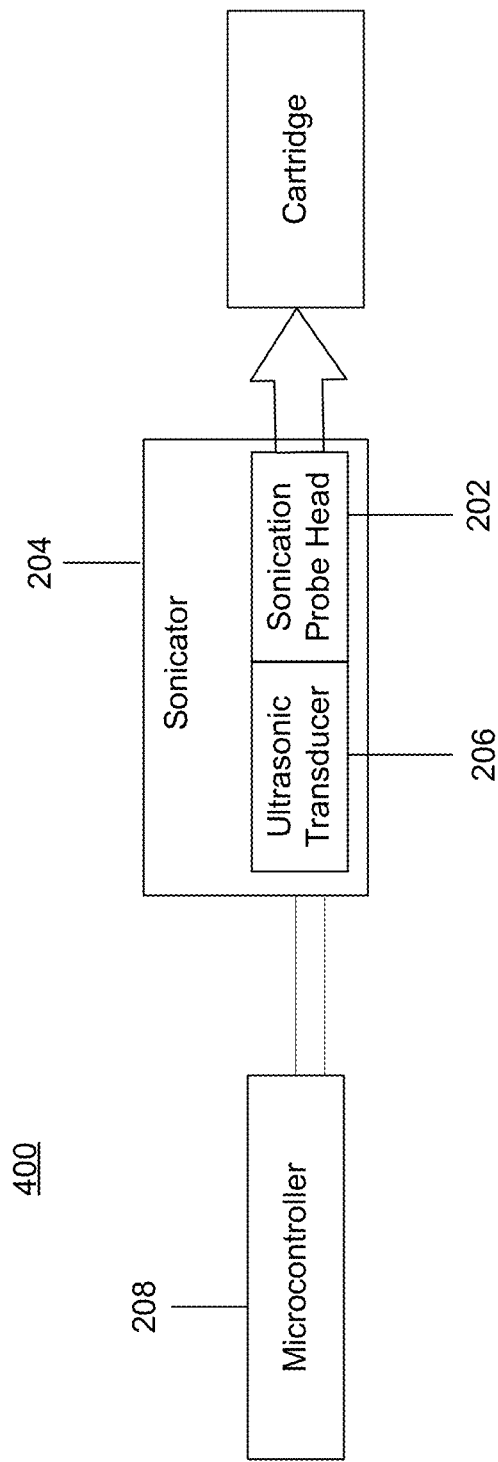
FIG. 4 is a block diagram of an example external sonicator system.

FIG. 4 shows a block diagram for an external sonicator system 400. The external sonicator system 400 is similar to the external sonicator system 200 except the external sonicator system 400 does not include any system or sample feedback. In one embodiment, the parameters of the external sonication system 400, as set and controlled by the microcontroller 208, are fixed (i.e., the parameters do not change). Fixed control does not account for potential drift of control parameters during use and over time that would impact disruption effectiveness. In one embodiment, the parameters of the external sonication system 400, as set and controlled by a microcontroller 208, are variable (i.e., one or more of the parameters change). Variable control allows for automated adjustments that adjust for potential drift of control parameters during use and over time that would impact disruption effectiveness.

The external sonicator systems 200, 400 can be used in any orientation on the cartridge, such as top sonication, bottom sonication, side sonication, or combinations thereof. Furthermore, the external sonication systems 200, 400 can include probe head touch control, such that the external sonication systems automatically turn on when the probe head is in contact with the cartridge and automatically turn off when the probe head is no longer in contact with the cartridge. Alternatively, the external sonication systems can be turned on and off based on a force exerted by or on the probe head.

Figure 5:
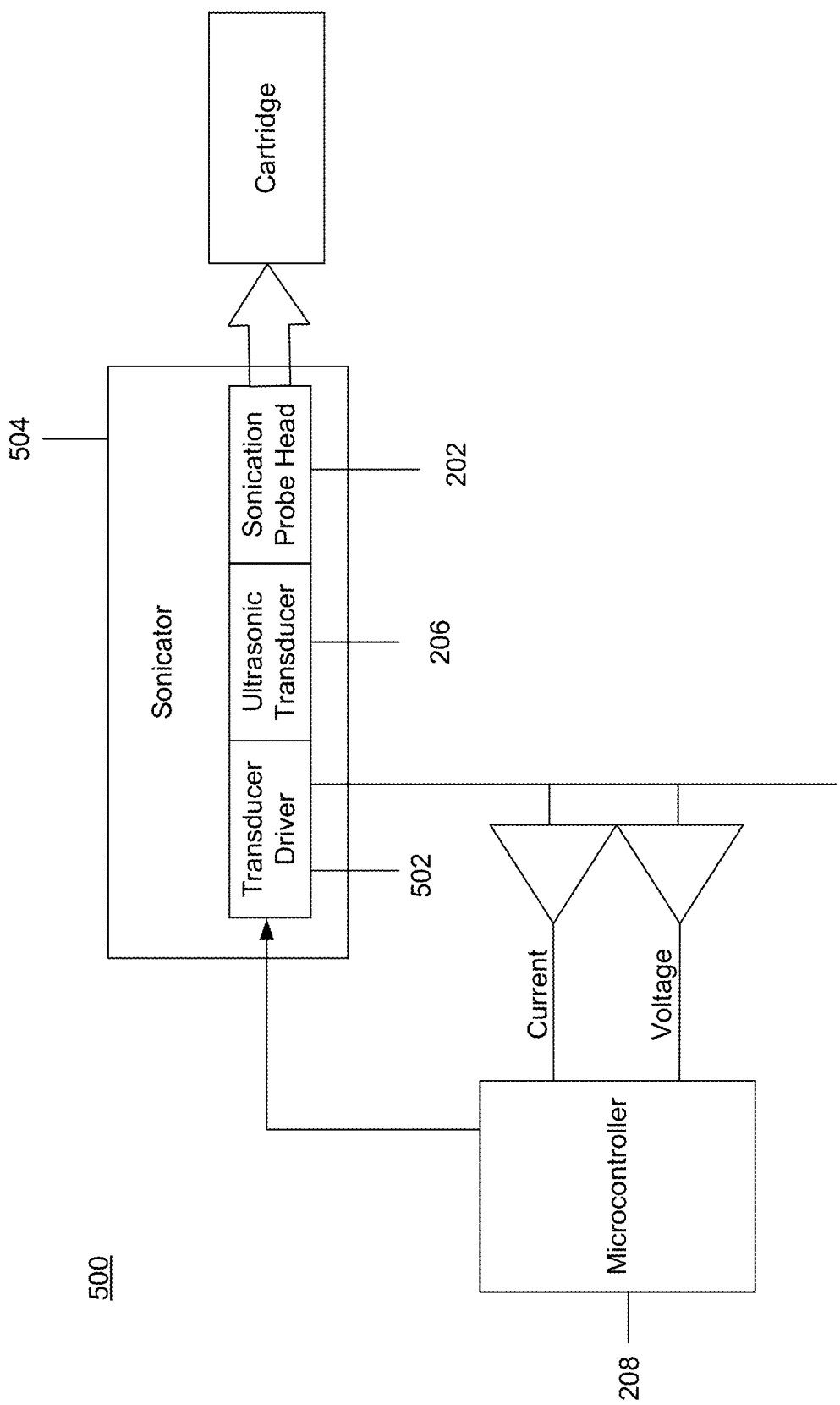
FIG. 5 is a block of an example driver.

The frequency can be adjusted manually or automatically, such as by a closed loop feedback. FIG. 5 shows an example driver 508 including a feedback loop for resonant compensation of an external sonicator system 500. The driver 508 defines the maximum power delivery for each sonication cycle and adjusts the frequency based on a closed loop feedback for each sonication cycle as the estimated shift of the resonance point of the ultrasonic transducer 506 due to effects of pressure/force or temperature on the probe head 502 and also due to contact mechanical resonance of the system considering the ultrasonic transducer 506 and the cartridge 800. The frequency can be adjusted for each cycle or for some cycles.

A method to determine the maximum power delivery each time cycle and adjusting the frequency to compensate for the estimated shift of the resonance point of the ultrasonic transducer 1006 due to effects of pressure force on the probe head 502 and contact mechanical resonance of the system considering the ultrasonic transducer 506, the probe head 502, and the cartridge 800 can also be implemented. The driver 508, during every pulse start cycle, defines the resonate point of the setup by sweeping through known deviations frequencies (i.e., deviation from a center frequency during operation over time by a given frequency) and looking for maximum power or targeted power (i.e., power at a specific or pre-determined amplitude) delivery though a defined proportional-integral-derivative (PID) loop (i.e., continuous calculation of an error value based on the difference between a desired setpoint and a measured process variable and application of a correction) to adjust to the lowest error defined from the theoretical calculation based on LC resonance (i.e., inductor and capacitor) defined by the drive circuitry. The loading effect and a non-functional transducer is detected by measuring the current at a known resonate point which can define a non-functional/overloaded ultrasonic transducer. The approximation is done by measuring the high side current of the driver circuit and based on statistical data for a given transducer approximates for functional ranges of current draw.

In one embodiment, the sonicator 504 uses a controlled voltage for the ultrasonic transducer 506 to control the total energy transfer to the cartridge 800 holding the cells or materials that needs to be lysed or disrupted—as non-controlled drive can result in an over-lysed (i.e., burned) or under lysed sample. The effectiveness of the lysing or disrupting can be at least partially attributed to the overall mixing of the solution and the sample, which is achieved by fast pulsing of the transducer controlled by electronics with effective pulse-width modulation (duty cycle) in order to control total power delivery to the ultrasonic transducer 506.

For example, the amount of lysing can be increased, even at the same frequency and with less power, by including a multi-layered piezoelectric element in the sonicator.

Performance of the external sonication system 500 is dependent on operation of the external sonication system 500 at the resonate point of the external sonication system 500. Operating the external sonication system 500 at the resonate point reduces energy loss and heat generation, whereas operating off the resonate point can damage the sample or the external sonication system 500 due to the generation of excessive heat and sound. The resonate point is impacted by one or more parameters, such as frequency, contact force, surface contact area, and temperature.

Figure 6A:
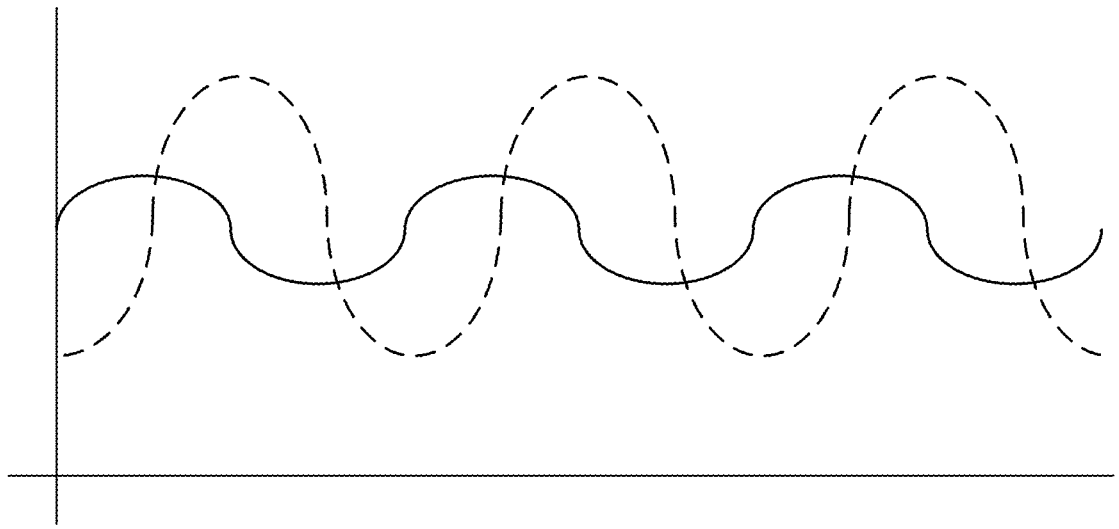
FIG. 6A illustrates an example out-of-phase waveform for a resonate point.
Figure 6B:
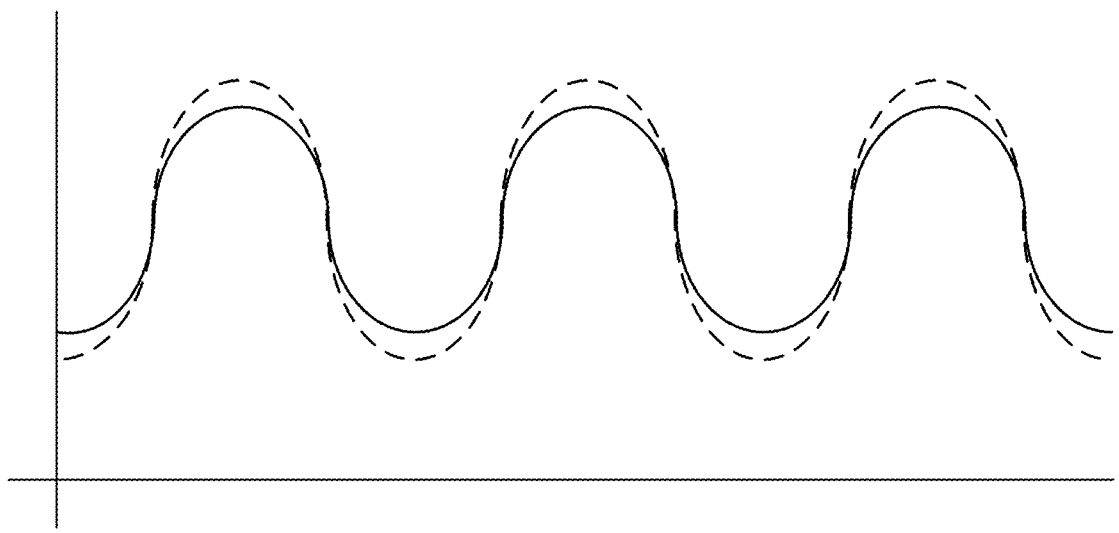
FIG. 6B illustrates an example in-phase waveform for a resonate point.

FIGS. 6A-6B show waveforms of the external sonication system 1000. In FIGS. 6A-6B, the solid line represents the measured voltage and the dashed line represents the measured current. In FIG. 6A, the external sonication system 1000 is not operating at the resonate point—the voltage and current are out of phase. Therefore, the energy being delivered is not optimized. In FIG. 6B, the external sonication system 1000 is operating at the resonate point—the voltage and current are in phase. Therefore, the energy being delivered to the sample is optimized. The y-axis represents amplitude and the x-axis represents time.

In one embodiment, searching for a resonate point is performed by measuring the current or voltage driving the ultrasonic transducer when sweeping across the ultrasonic transducer frequency and voltage. The voltage and frequency which result in the measured peak current, which is the resonate point are used by the drive circuit thereby resulting in the maximum energy deliverable into the cartridge at the lowest energy loss.

Furthermore, the resonate point can be maintained or changed by pre-warming the sonicator 204 by turning on the ultrasonic transducer 206 before the sonicator 204 is brought into contact with the cartridge 800; by pre-loading a contact force of the sonicator 204 on the cartridge 800 by applying the sonicator 204 to a cartridge wall before turning on the ultrasonic transducer 206; by pulsing the contact force of the sonicator 204 on the cartridge 800 when turning on the ultrasonic transducer 206; or, during the external sonication process, using variable contact force of the sonicator 204 based on measured ultrasonic transducer energy being consumed to optimize energy transfer into the sample.

To measure that the external sonication system is operating within acceptable specifications, changes in the voltage, current, temperature, frequency, or combinations thereof can be measured and a threshold can be set to determine when the resonate point of the system has drifted outside of functional specification settings for each of the above.

However, it should be noted that switching between being operating at the resonate point and operating off the resonant can be advantageous. In one aspect, switching between operating on and off the resonate point can increase sample temperature. In another aspect, switching between operating on and off the resonate point can mix or agitate the sample without heating or causing disruption of the contents of the sample.

Figure 7A:
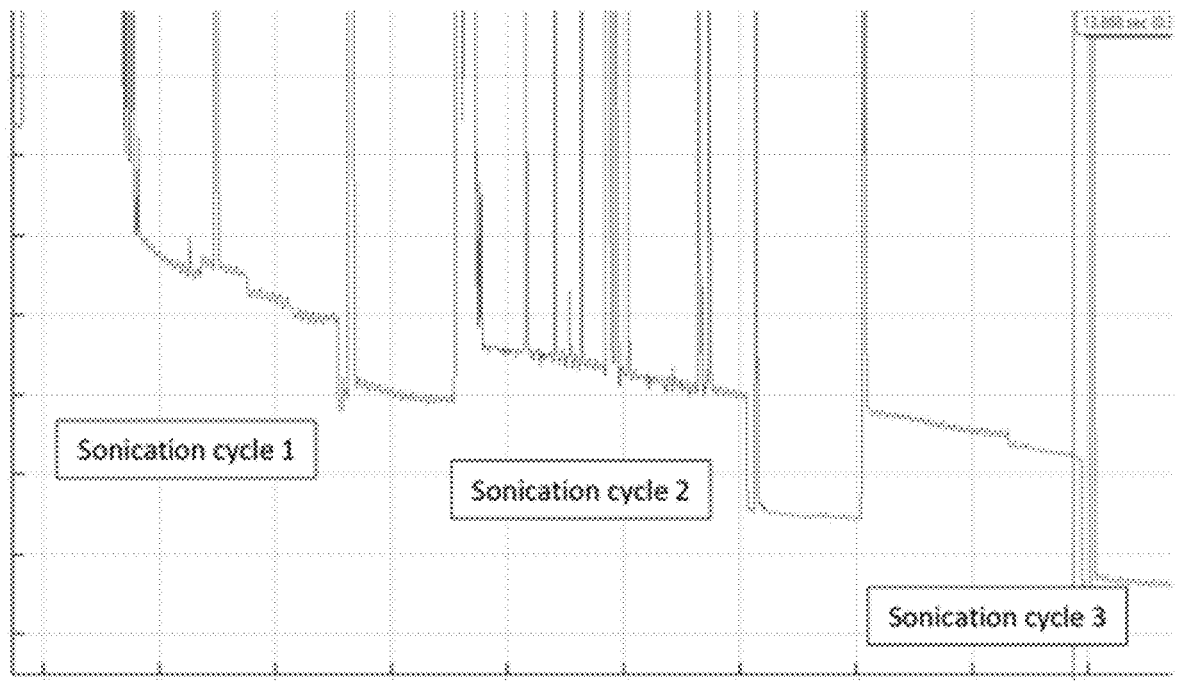
FIG. 7A illustrates an example non-desired sonication waveform.
Figure 7B:
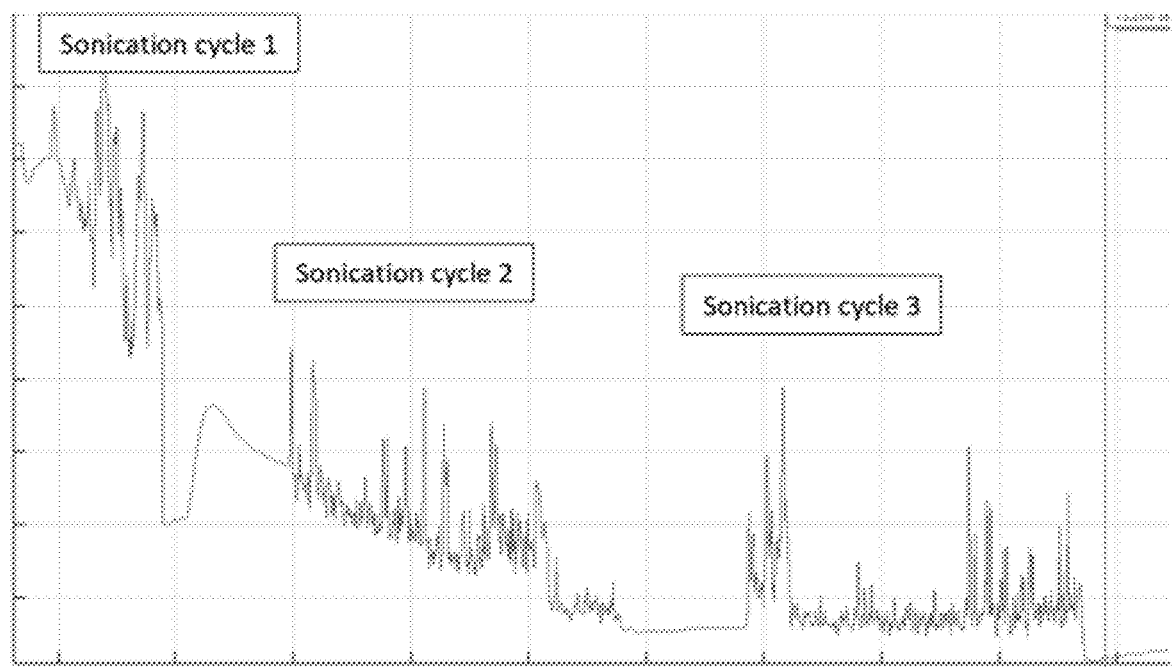
FIG. 7B illustrates an example desired sonication waveform.

FIGS. 7A-7B illustrate waveforms showing non-desired sonication and desired sonication, respectively. To determine whether the sonication is desirable or non-desirable, sample opacity can be measured before, during, and after sonication. Alternatively, or in addition to the measurements, one or more algorithms can be employed which determined absolute or relative changes in the sample opacity before sonication and after sonication, and sample opacity change during sonication.

As shown in FIG. 7A, when measuring changes in sample opacity before, during, and after the external sonication process a very small change in voltage is observed (i.e., <30 mV) and very little change of signal from the sample is observed during the external sonication process. This waveform signature typifies undesirable external sonication of the sample as there is minimal change in opacity and minimal opacity agitation during the external sonication process. This information is then used by the system to determine if additional external sonication should be applied or if the process should proceed. In the example provided in FIG. 7A, additional external sonication would be performed or a notification would be provided that the external sonication was successful or failed, such that the sample would not proceed to the next step—at least until proper external sonication has occurred. When the external sonication, as performed, provides non-desirable results, the external sonication can be repeated and the control parameters can be adjusted to achieve desirable results.

As shown in FIG. 7B, the waveform signature typifies desirable external sonication in the sample as there is a large change in opacity and large opacity agitation during sonication process. In this example, the system measures changes taking place within the sample before, during, and after the external sonication process. In this example, when measuring changes in sample opacity before, during, and after external sonication, a very large change in voltage is observed (i.e., >300 mV, which is 10× the change observed in FIG. 7A) and very large change of signal from sample is observed during the external sonication process. This information is then used by the system to determine if additional external sonication should be applied or testing should proceed. In the example provided in FIG. 7B, additional external sonication need not be performed and the sample can proceed to the next step of testing or processing.

A sonication algorithm can be used to increase the efficiency, effectiveness, or both of a sonicator, such as the sonicator 200. The sonication algorithm determines a sonication frequency, such as an optimal sonication frequency, by starting at a first frequency (e.g., 50 kHz) and adjusting the frequency, such as by sweeping or incrementing, by a given interval (e.g., 200 Hz intervals). The sonication algorithm also calculates or determines a maximum current (e.g., >500 mA) delivered to the sonicator from the sample, which indicates a resonance point.

To account for system to system variability (i.e., variability between sonicators, between detection system, between sample readers, between analysis devices or systems, or the like), the sonicator can be set to a pre-determined frequency. The variability can be due to differences in one or more cartridges (e.g., due to manufacturing processes), sonicator assembly elliptical characteristics, force of the sonicator head against the cartridge, the like, or combinations thereof.

The sonication algorithm also includes an on/off control to increase sonication efficiency while reducing sample damage and cartridge damage. Total time, durations, pause duration, number of pauses, number of pulses, the like, or combinations or multiples thereof are considered. In one example, the sonication algorithm includes rest periods (e.g., every 25-40 ms) during an active run (e.g., 2-3 secs) to eliminate local hot spots and prevent cell damage. Longer pauses (e.g., 2-5 seconds) can be used for a cooling period. The rest periods (e.g., 25-40 ms) can be used to break up collection of fluids due to coagulation, surface tension, friction, viscosity, the like, or combinations or multiples thereof.

An example sonication algorithm can be used in reference to a round sonicator probe head to control energy coupling by directing energy into a cartridge surface. The sonication algorithm alternates between one of two operating frequencies (e.g., main frequency or main frequency and higher cavitation seeding frequency) and "off" (i.e., no frequency). The sonication algorithm also switches between a second resonate point at a higher frequency and a nominal resonate frequency, such that the higher frequency enables smaller cavitation bubbles to seed larger bubble formation or collapse for lysing. The sonication algorithm also runs at a duty cycle of 50% to enable to cartridge and sample to rest to allow for heat dissipation and elimination of local hot spots.

The sonication algorithm can also use a lower frequency, on/off periods, or both to facilitate fluidic movement, thereby mixing at least two substances, including the sample and a solution or reagent.

Figure 8A:
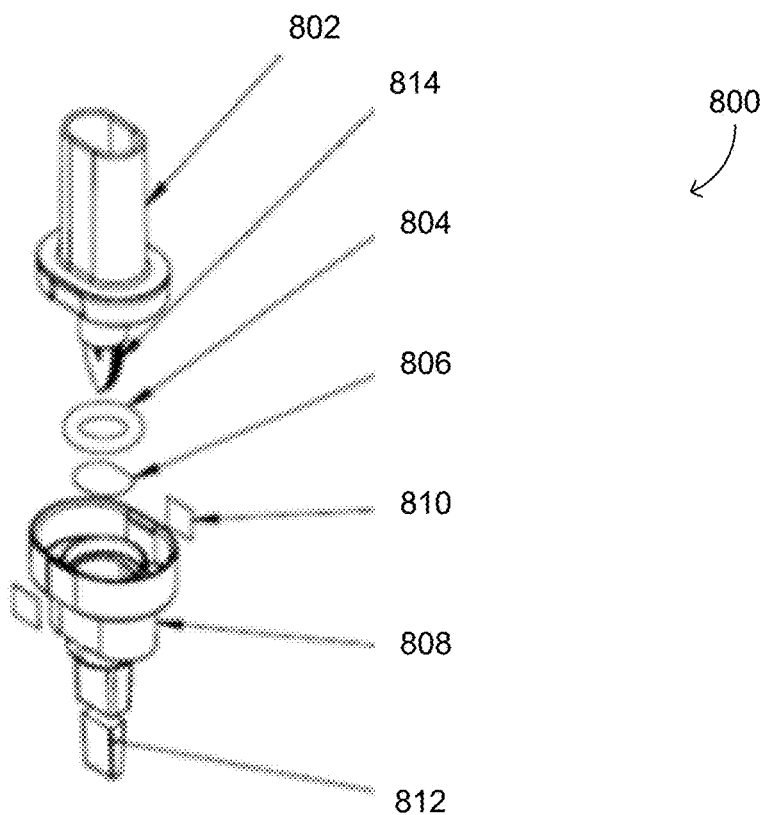
FIG. 8A illustrates an exploded view of an example cartridge.
Figure 8B:
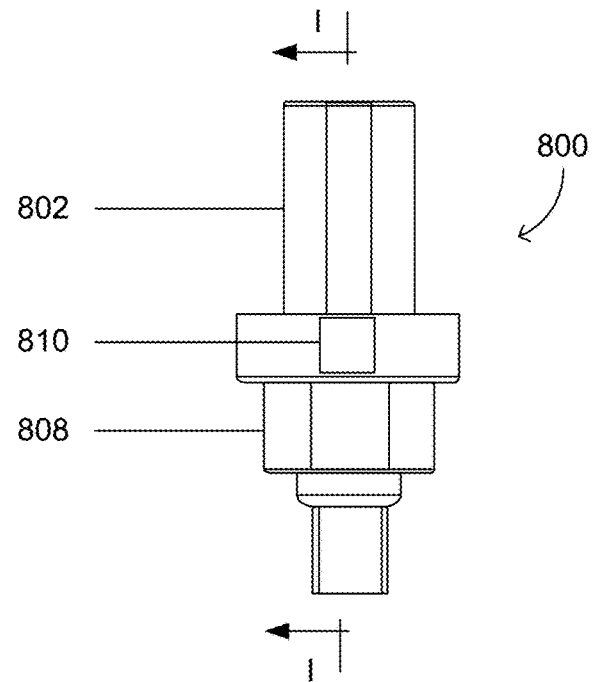
FIG. 8B illustrates the example cartridge.

FIG. 8A shows an exploded view of an example cartridge 800 in which to store and sonicate a sample. FIG. 8B shows an isometric view of the example cartridge 800. The cartridge 800 includes a capillary 802 having a capillary plane and first and second ends, an O-ring 804, a membrane 806, and a cuvette 808 having first and second ends. The cartridge 800 can also include at least one of a label 810 or a reagent 812. In one embodiment, the cartridge 800 can be sealed. For example, the cartridge 800 is sealed to the external environment. In yet another example, the cartridge can be sealed permanently or temporarily.

The capillary 802 draws the blood sample into the cartridge 800 via capillary action or captures a fixed volume of a sample from a drop of blood. The capillary plane of the capillary 802 pierces the membrane 806 of the cuvette 808 when the capillary 802 and the cuvette 808 are adjoined, such as during a latching process or the snapping process. The capillary 802 can include a capillary coating 814 to enhance wicking of the sample through the capillary 802. In one embodiment, the sample can be added, such as by pipetting, pouring, or the like, directly into the cuvette 808. The sample can include one or more reagents, one or more sonication particles, or one or more reagents and one or more sonication particles.

In one embodiment, the capillary 802 and the cuvette 808 are one piece. In one embodiment, the capillary 802 and the cuvette 808 are separate pieces. The cuvette 808, for example, latches with one or more other components of the cartridge 800. Additionally, the capillary 802, for example, latches with one or more other components of the cartridge 800. Alternatively, the cuvette 808 and the capillary 802 can be snapped together, and, once snapped together, do not come apart. Though the cartridge 800 is discussed as including the capillary 802, the cartridge 800 can be formed without the capillary 802 or with another mechanism to get or transfer the material or diluent into the cuvette 808.

The cuvette 808 is composed of a material or materials, such as glass, crystal, plastic, or combinations thereof, having optical properties allowing for the passage of light of a light source through the cuvette 808 and into the sample to collect information about the sample. For example, the cuvette 808 can be optically clear to allow for the imaging or data collection. In another example, the cuvette 808 can be transparent, semi-transparent, or translucent. In yet another example, the material can be selected based on a certain wavelength to be filtered out or to be passed through to the sample.

The first end of the cuvette 808 can include the membrane 806. The membrane 806 seals the reagent 812 in the cuvette 808 to prevent spillage, for storage purposes, to contain the sample during external sonication, or to be used at a later time. The seal of the membrane 806 can be formed by heat stake with mandrel, hot heat stake with precise volume, hot heat staking with reagent overfill in the cuvette 808, or cold to hot heat staking with reagent overfill or other methods to seal fluids in the cuvette 808. Furthermore, the membrane 806 can include a hydrophilic coating, which changes the shape of a meniscus of the reagent 812 during the heat staking process.

The second end of the cuvette 808 can include a fluid chamber which holds the reagent 812, the sample, or a combination thereof. The cuvette 808 can also include a given volume of the reagent 812 or sample. The reagent can include, without limitation, deionized water, surfactants, defoaming agent, stains (e.g., fluorescent, chromogenic, or the like), or the like. In one embodiment, 2% Triton (i.e., a surfactant; a nonionic surfactant that has a hydrophilic polyethylene oxide chain and an aromatic hydrocarbon lipophilic or hydrophobic group) is used as a reagent (e.g., to optimize external sonication), a capillary coating (e.g., to enhance sample collection and wicking), and to release hemozoin, when it is desirous to do so. In another embodiment, a plurality of reagents can be used. For example, a surfactant and a stain can be used.

In one embodiment, the cuvette 808 can also include at least one sonication particle to increase mixing, enhance sonication, or increase mixing and enhance sonication. The at least one sonication particle can be composed of glass, a polymer, a metal, silica, combinations thereof, or the like. For example, 16 glass beads are added to the sample, such as blood, to increase mixing and to enhance sonication. In one embodiment, when two or more sonication particles are included, no two sonication particles are composed of the same material, such that at least one sonication particle is composed of a first material and at least one sonication particle is composed of a second material. In another embodiment, when two or more sonication particles are included, all of the sonication particles are composed of the same material, such that the two or more sonication particles are composed of a first material. Alternatively, the at least one sonication particle can be added to the sample before being added to the cuvette 808.

The O-ring 804, which can be on the capillary 802 or the cuvette 808, provides a seal between the capillary 802 and the cuvette 808 when the capillary 802 and the cuvette 808 are latched or snapped together. The seal provided by the O-ring 804 can be fluid and air tight.

The thickness and shape of the walls of the cartridge 800 are two parameters which impact the transfer of the ultrasonic energy. Therefore, an optimal wall thickness and the wall shape enhance ultrasonic energy transfer or make ultrasonic energy transfer more efficient. Additionally, the sonication probe head 1404 design enhances ultrasonic energy transfer based on the material type of the cartridge 800, the wall thickness of the cartridge 800, the wall shape of the cartridge 800, or combinations thereof.

The label 810 includes a control number which can be encoded through an encryption algorithm to a second number. At least one batch number, revision number, or serial number, whether in whole or in part, can be encrypted. The control number can also include a manufacturing date to prevent use after an expiration date. The label 810 can also include a design, such as a graphic, code (e.g., QR code), or image, which can be visible to the human eye or only visible to a machine or via another visualization system. The design can include encrypted data.

In one embodiment, one or more machines, such as the external sonication system 1100 or the reader 100, 140, do not work when the number having been encrypted is incorrect (i.e., number being encrypted does not fit a desired or proper format or does not correspond with the unencrypted number), has been used already, or is not found in a lookup table. This prevents reuse of the cartridge 800 or use of uncertified cartridges. The one or more machines record each cartridge used, such as on internal storage, and upload the sequence numbers to a server or table, which can be internal to the machine or remotely connected, such as in the cloud. The used sequence numbers can be downloaded to all machines when connected to the cloud or remote server to prevent reuse in different machines or to prevent the use of a copied label or sequence number. Alternatively, a remote server can receive all used sequence numbers and identify those sequence numbers that are used more than once, including twice or more. The remote server can compare the sequence number to a database or lookup table. Those used more once, such as twice or more, can be automatically pushed to one or more machines based on location of the machine, frequency of use of the machine, proximity of the attempted counterfeit uses on other machines, or the like. An application, such as one loaded onto the machine or stored in the cloud, can be used to examine data for duplicate sequence numbers and flag them for review, such as by a human or other application.

As another way to prevent reuse, the label 810 or another portion of the cartridge 800 can include at least one of an electrical fused link. As yet another way to prevent reuse, the label 810 or another portion of the cartridge 800 can be marked, scratched, color changed, physically changed (e.g., dimples, pop-ins, or the like), or combinations thereof.

An electronic tag (e.g., IC tag) or RFID tag can be included on the label 810 or another portion of the cartridge 800.

A custom designed cartridge that works with a second device locks into the second device, such that all degrees of freedom are constrained to reduce the chance of the fluid sample/medium from vibrating or sloshing, which allows for lower noise and higher sensitivity measurements of the sample volume.

Figure 8C:
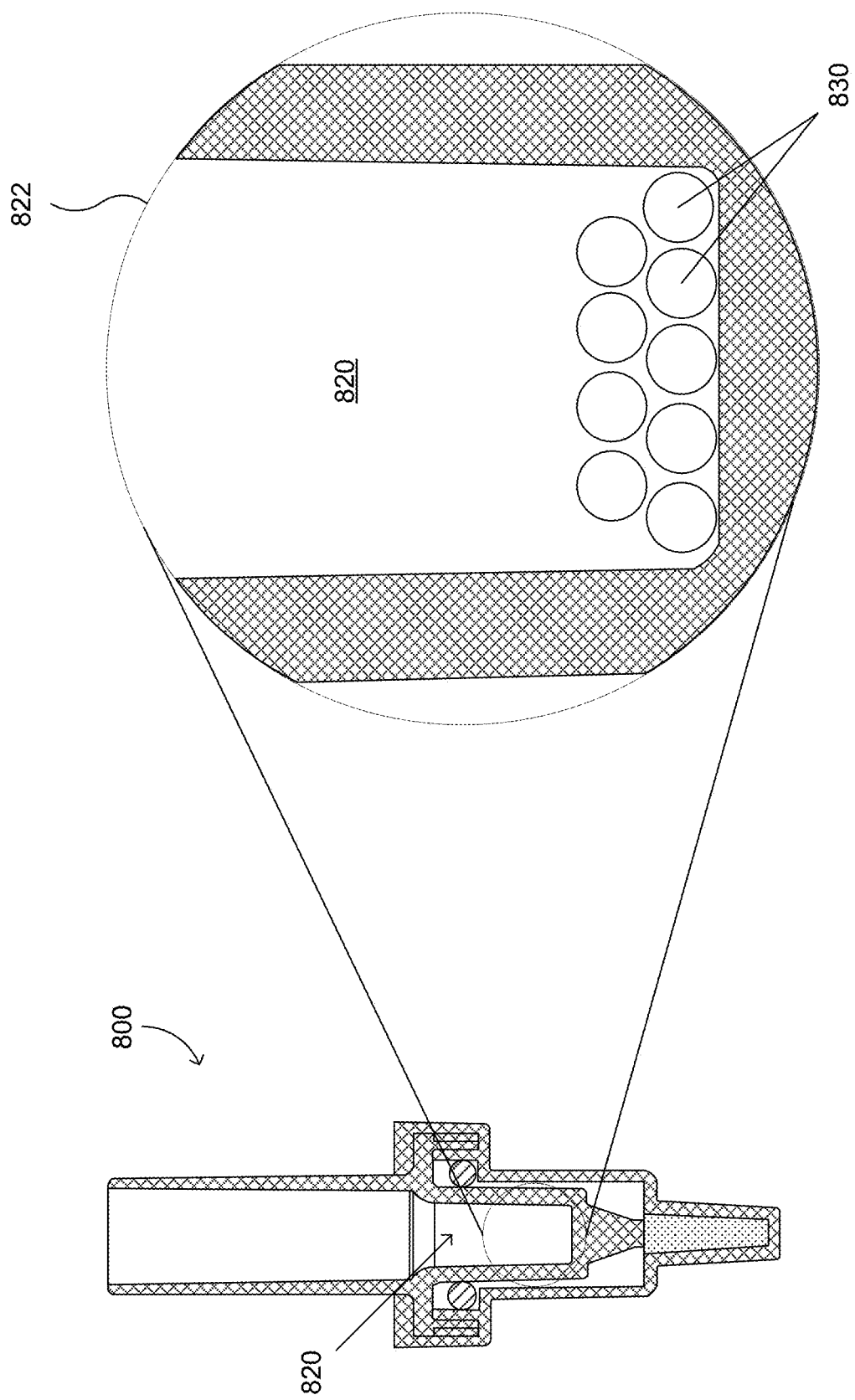
FIG. 8C illustrates a cross-sectional view of the example cartridge.

FIG. 8C shows a cross-section view of the cartridge 800 taken along line I-I. The cartridge 800 includes a sonication chamber 820 in which the sample is added or located to undergo sonication. The sonication chamber 820 can include sonication particles 830, as shown in magnified view 822. The sonication particles 830 improve or enhance sonication, sample mixing, or both. Any number of sonication particles 830 can be used (e.g., up to 1000, including 20-30) and the sonication particles 830 can be any appropriate size (e.g., up to 10 mm, including 0.6 mm, 1 mm, or the like).

The sonication particles 830 can have a density or size to drop to the bottom of the sample when sonication is stopped. The sonication particles 830 can mechanically lyse the sample component through movement of the sonication particles 830, seed cavitation bubble formation, or both.

In one example, the sonication particles 830 provide an increased surface area on which cavitation can occur (i.e., seeding point for cavitation). During sonication, cavitation can occur whereby air bubbles are formed within the sample. The bubbles, having energy (e.g., kinetic energy), can agitate or disrupt sample components (i.e., breaking apart a membrane, vacuole, or the like). In another example, the sonication particles 830, being agitated by the sonication, can move around within the sample. The sonication particles 830 contact the sample components and agitate or disrupt the sample components (i.e., breaking apart the membrane, vacuole, or the like).

In one example, the sonication particles 830 can be added to the sonication chamber 820 before adding the sample. The sonication particles 830 can be adhered to an inner wall of the sonication chamber 830, such as by coating the sonication particles 830 in an adhesive or sticky solution, such as a Triton solution, before addition to the sonication chamber 830. When dried, the sonication particles 830 retain a sticky residue. The sonication particles 830 are can be unstuck from the cartridge 800 before sonication with one or more reagents or by the sample itself. The reagent or solution can lyse the sample component on its own.

In another example, the sonication particles 830 can be added to the sample before the sample is added to the cartridge 800.

An example for adhering sonication particles 830 to the sonication chamber 820 includes adding the sonication particles 830 to the sonication chamber 820, adding a reagent (e.g., 2 µL of 2% Triton), and drying (e.g., air dry, curing, or heated dry). The sonication particles 830 are then coated in a residue which adheres the sonication particles 830 to the inner wall of the sonication chamber 820.

The cartridge 800 can also include a cavitation seeder, such as a cut, a ridge, a knit line, the like, or combinations or multiples thereof, to seed cavitation. The cartridge 800 can include the cavitation seeder and the sonication particles 830.

Though certain elements, aspects, components or the like are described in relation to one embodiment or example, such as an example external sonication system, those elements, aspects, components or the like can be including with any other external sonication system, such as when it desirous or advantageous to do so.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents.

What is claimed is:

1. An external sonication system for sonicating a patient sample stored in a patient sample cartridge, the patient sample cartridge having an external wall, the system comprising:
   an external sonicator comprising:
      an ultrasonic transducer coupled to a probe head having an external surface,
      wherein, when the external surface of the probe head comes into direct physical contact with the external wall of the patient sample cartridge, the direct physical contact creates a probe head contact force between the probe head and the patient sample cartridge; and
   a microcontroller electrically coupled to the external sonicator, the microcontroller configured to:
      generate a signal to control a characteristic or parameter of the ultrasonic transducer,
      transmit the signal to the ultrasonic transducer, and
      cause the ultrasonic transducer to generate ultrasonic energy based on
   the characteristic or parameter and to transmit the generated ultrasonic energy through the external wall of the patient sample cartridge based on the probe head contact force between the external surface of the probe head and the external wall of the patient sample cartridge.

2. The system of claim 1, wherein the external surface of the probe head is shaped to mate with the external wall of the patient sample cartridge.

3. The system of claim 1, wherein the ultrasonic transducer is coupled to the probe head with a non-dampening or non-resonant-point-changing pressure or force.

4. The system of claim 1, wherein the probe head has a length proportional to or matched to a resonate frequency of the ultrasonic transducer.

5. The system of claim 1, wherein the external sonicator is configured to be oriented in one of multiple orientations.

6. The system of claim 1, wherein the microcontroller is programmed to control the characteristic or parameter of the ultrasonic transducer based on at least one of:
location of the probe head relative to the external wall of the patient sample cartridge,
probe head contact force of the probe head against the external wall of the patient sample cartridge,
sample sonication feedback,
user input settings, and
manufacturing assembly feedback.

7. The system of claim 1, wherein the characteristic or parameter of the ultrasonic transducer is fixed or variable.

8. The system of claim 1, wherein the characteristic or parameter of the ultrasonic transducer is ultrasonic energy transfer efficiency, fixed or variable frequency, on or off sonicator probe resonate point, temperature, applied voltage, current, voltage on/off time, current on/off time, or combinations or multiples thereof.

9. The system of claim 1, wherein the microcontroller is further configured to determine resonate point drift outside of a functional frequency of the ultrasonic transducer by measuring changes to current, voltage, frequency, temperature, or combinations thereof.

10. The system of claim 1, wherein the microcontroller is further configured to control a position and the probe head contact force of the external sonicator against the external wall of the cartridge.

11. The system of claim 1, wherein the microcontroller is further configured to transmit the ultrasonic energy into the cartridge by varying the voltage or current applied to the ultrasonic transducer in a fixed or random frequency that is proximal to a resonate point of the ultrasonic transducer.

12. The system of claim 1, wherein the microcontroller is further configured to cause a voltage or current applied to the ultrasonic transducer to be reduced or increased to adjust transmission of the ultrasonic energy into the cartridge.

13. The system of claim 1, wherein the microcontroller is further configured to cause a voltage or current applied to the ultrasonic transducer to be pulsed to increase transmission of the ultrasonic energy into the cartridge.

14. The system of claim 1, wherein the microcontroller is further configured to one or both of:
cause a voltage or current applied to the ultrasonic transducer to be turned off when a temperature of the ultrasonic transducer exceeds a heat threshold; and
cause the voltage or current to be turned on when the temperature of the ultrasonic transducer reaches a cool threshold.

15. The system of claim 1, wherein the microcontroller is further configured to determine a resonate point of the ultrasonic transducer by measuring a frequency and a voltage at which a peak current occurs when driving the ultrasonic transducer with variable frequency and variable voltage.

16. The system of claim 1, wherein the microcontroller is further configured to pre-warming the ultrasonic transducer by turning on the ultrasonic transducer before the external sonicator is brought into contact with the external wall of the cartridge.

17. The system of claim 1, wherein the microcontroller is further configured to generate a signal to switch the ultrasonic transducer from being on a resonate point to off the resonate point.

18. The system of claim 1, wherein the microcontroller is further configured to compare an opacity of the patient sample at a first time to an opacity of the patient sample at a second time, and
cause the signal to change the characteristic or parameter of the ultrasonic transducer in response to a change in the opacities of the patient sample from the first time to the second time.

19. The system of claim 1, wherein the microcontroller is configured to:
cause control parameters to be adjusted;
cause a failure notification of sonication to be output;
cause a successful notification of sonication to be output; or
combinations or multiples thereof.

20. The system of claim 1, wherein the microcontroller is further configured to:
determine resonate point drift of the ultrasonic transducer outside of a functional specification, and
cause the ultrasonic transducer to operate within the functional specification by changing the characteristic or parameter of the ultrasonic transducer with the signal.

21. The system of claim 1, wherein the microcontroller is further configured to
adjust a frequency of the ultrasonic transducer based on a closed loop feedback for a cycle to compensate for an estimated shift of a resonate point of the ultrasonic transducer based on an effect of the probe head contact force or a temperature on the probe head and a contact mechanical resonance of the external wall of the patient sample cartridge.

22. The system of claim 1, wherein the microcontroller is further programmed to:
calculate a resonate point of the ultrasonic transducer at the start of a pulse cycle, and
adjust the characteristic or parameter of the ultrasonic transducer to obtain a lowest error of a proportional-integral-derivative (PID) loop.

23. The system of claim 21, wherein the microcontroller is further configured to identify a non-functioning or overloaded state of the ultrasonic transducer by
measuring a high side current of a drive circuitry,
comparing the high side current against functional ranges of current draw at one or more known resonant frequencies of the ultrasonic transducer, and
adjust a frequency of the ultrasonic transducer to change the ultrasonic transducer from the non-functioning or overloaded state to a functioning state.

24. The system of claim 1, wherein the microcontroller is further configured to cause a contact force of the external sonicator to be pre-loaded by applying the probe head of the external sonicator to the external wall of the cartridge before the ultrasonic transducer is turned on.

25. The system of claim 1, wherein the microcontroller is further configured to cause the contact force of the external sonicator to be pulsed when turning on the ultrasonic transducer.

26. The system of claim 1, wherein the microcontroller is further configured to cause the contact force of the external sonicator to be varied.

* * * * *